(12) United States Patent
Ito et al.

(10) Patent No.: US 8,293,771 B2
(45) Date of Patent: *Oct. 23, 2012

(54) P38 MAP KINASE INHIBITORS

(75) Inventors: Kazuhiro Ito, London (GB); Peter Strong, London (GB); William Garth Rapeport, London (GB); John King-Underwood, Pendock (GB); Jonathan Gareth Williams, Nottingham (GB); Stuart Thomas Onions, Nottingham (GB); Peter John Murray, London (GB); Catherine Elisabeth Charron, London (GB)

(73) Assignee: Respivert Ltd. (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/121,445

(22) PCT Filed: Oct. 2, 2009

(86) PCT No.: PCT/GB2009/051303
§ 371 (c)(1),
(2), (4) Date: Mar. 29, 2011

(87) PCT Pub. No.: WO2010/038085
PCT Pub. Date: Apr. 8, 2010

(65) Prior Publication Data
US 2011/0269800 A1    Nov. 3, 2011

(30) Foreign Application Priority Data
Oct. 2, 2008   (GB) .................................. 0818033.3

(51) Int. Cl.
*A61K 31/4427* (2006.01)
*C07D 401/02* (2006.01)
(52) U.S. Cl. ..................................... 514/340; 546/275.4
(58) Field of Classification Search .................. 514/340; 546/275.4
See application file for complete search history.

(56) References Cited

U.S. PATENT DOCUMENTS

| | | |
|---|---|---|
| 6,525,046 B1 | 2/2003 | Cirillo et al. |
| 6,916,814 B2 | 7/2005 | Moss et al. |
| 7,329,670 B1 | 2/2008 | Dumas et al. |
| 7,625,915 B2 | 12/2009 | Dumas et al. |
| 2004/0180906 A1 | 9/2004 | Flynn et al. |
| 2004/0192653 A1 | 9/2004 | Munson et al. |
| 2007/0010529 A1 | 1/2007 | Takahashi et al. |
| 2008/0113967 A1 | 5/2008 | Flynn et al. |
| 2008/0207699 A1 | 8/2008 | Hoelzemann et al. |
| 2008/0300281 A1 | 12/2008 | Dumas et al. |
| 2011/0212962 A1 | 9/2011 | Ito et al. |

FOREIGN PATENT DOCUMENTS

| | | |
|---|---|---|
| WO | WO 99-23091 | 5/1999 |
| WO | WO 99/32110 | 7/1999 |
| WO | WO 99/32111 | 7/1999 |
| WO | WO 99/32455 | 7/1999 |
| WO | WO 99/47529 | 9/1999 |
| WO | WO 00/43384 | 7/2000 |
| WO | WO 01/04115 | 1/2001 |
| WO | WO 02/066442 | 8/2002 |
| WO | WO 02/092576 | 11/2002 |
| WO | WO 03/005999 | 1/2003 |
| WO | WO 03/068228 | 8/2003 |
| WO | WO 03/072569 | 9/2003 |
| WO | WO 03/084503 | 10/2003 |
| WO | WO 2004/014387 | 2/2004 |
| WO | WO 2004/021988 | 3/2004 |
| WO | WO 2004/060306 | 7/2004 |
| WO | WO 2004/078746 | 9/2004 |
| WO | WO 2004/089929 | 10/2004 |
| WO | WO 2004/100946 | 11/2004 |
| WO | WO 2005/018624 | 3/2005 |
| WO | WO 2005/048948 | 6/2005 |
| WO | WO 2005/110994 | 11/2005 |
| WO | WO 2005/113511 | 12/2005 |
| WO | WO 2006/009741 | 1/2006 |
| WO | WO 2006/014290 | 2/2006 |

(Continued)

OTHER PUBLICATIONS

Friedenreich, Christine M. State of the epidemiological evidence on physical activity and cancer prevention. European Journal of Cancer, 46, (2010), 2593-2604.*
U.S. Appl. No. 13/133,998, filed Aug. 9, 2011, Ito et al.
U.S. Appl. No. 13/139,010, filed Aug. 9, 2011, Ito et al.
U.S. Appl. No. 13/262,266, filed Sep. 30, 2011, Ito et al.

(Continued)

*Primary Examiner* — Joseph K. McKane
*Assistant Examiner* — Samantha Shterengarts
(74) *Attorney, Agent, or Firm* — Mary A. Appollina

(57) ABSTRACT

There is provided a compound of formula (I) or a pharmaceutically acceptable salt or solvate thereof, including all tautomers thereof, compositions comprising the same, use of said compound and compositions for treatment, in particular for the treatment of asthma and COPD, and processes for the preparation of said compound.

(I)

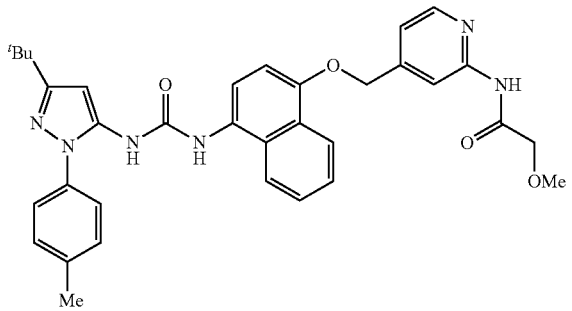

9 Claims, 2 Drawing Sheets

FOREIGN PATENT DOCUMENTS

| WO | WO 2006/015775 | 2/2006 |
| WO | WO 2006/028524 | 3/2006 |
| WO | WO 2006/043090 | 4/2006 |
| WO | WO 2006/062984 | 6/2006 |
| WO | WO 2006/068591 | 6/2006 |
| WO | WO 2006/072589 | 7/2006 |
| WO | WO 2006/081034 | 8/2006 |
| WO | WO 2007/002635 | 1/2007 |
| WO | WO 2007/017083 | 2/2007 |
| WO | WO 2007/038425 | 4/2007 |
| WO | WO 2007/059202 | 5/2007 |
| WO | WO 2007/064872 | 6/2007 |
| WO | WO 2008/016192 | 2/2008 |

OTHER PUBLICATIONS

Dumas et al., "Synthesis and Pharmacological Characterization of a Potent, Orally Active p38 Kinase Inhibitor", Bioorganic & Medicinal Chemistry Letters 12 (2002) 1559-1562.

International Search Report, PCT/GB2009/051303, dated Apr. 15, 2010.

* cited by examiner

FIGURE 1. Effect on LPS-induced neutrophil accumulation
[number of neutrophils in BAL]
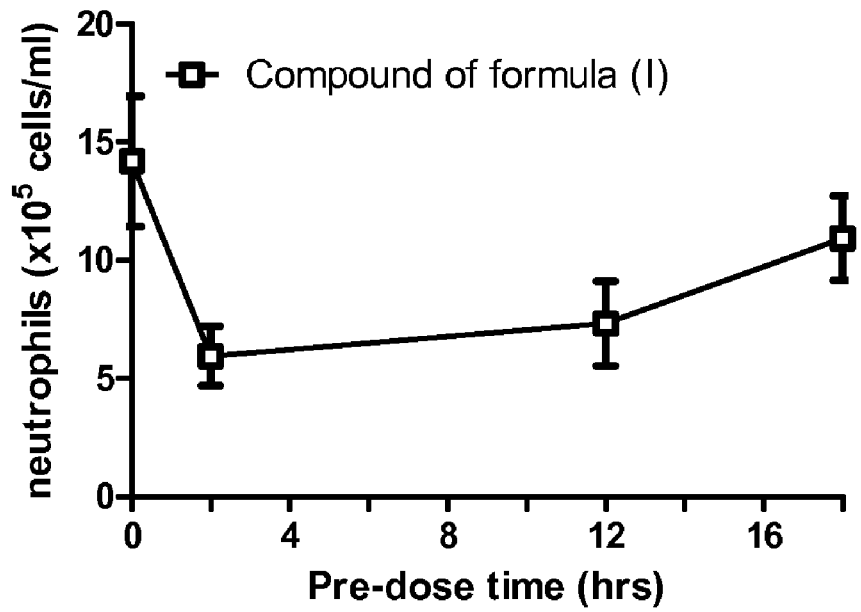
FIGURE 2. Effect on LPS-induced neutrophil accumulation
[inhibition %]
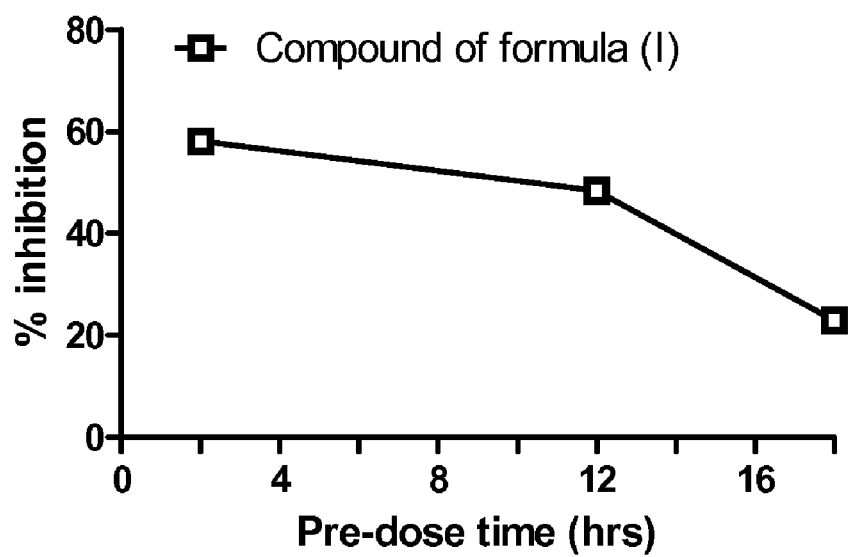

Figure 3: MOMA2⁺-Macrophage Accumulation in BALF
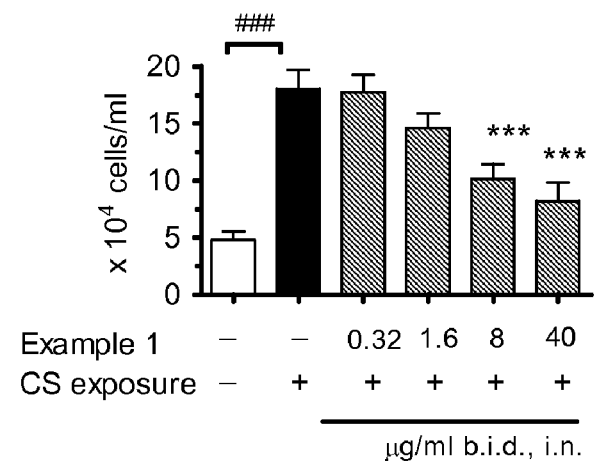
Figure 4: Neutrophil Accumulation in BALF
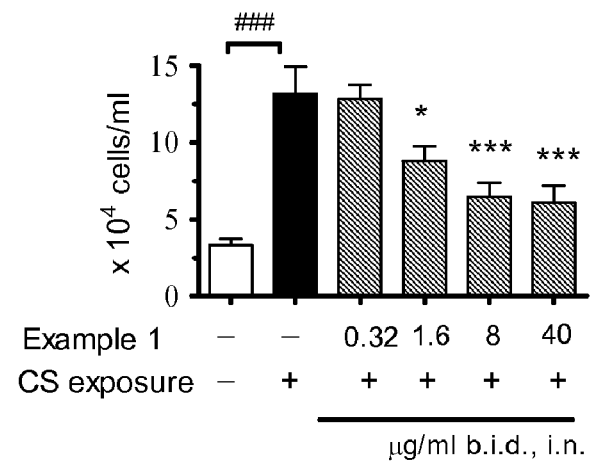
Figure 5
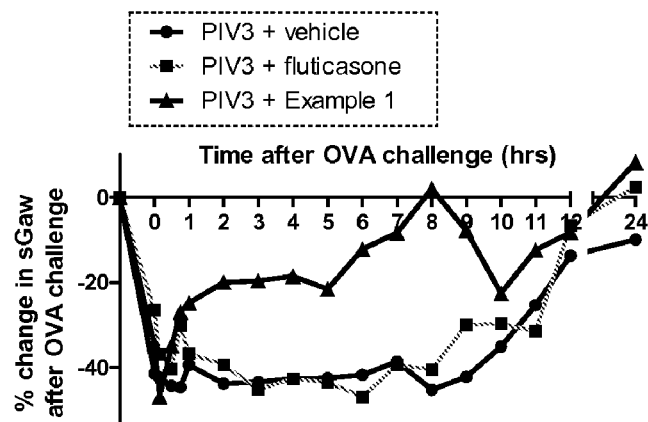

P38 MAP KINASE INHIBITORS

This application is a National Stage application under 35 U.S.C. 371 of PCT International Application No. PCT/GB2009/051303, filed Oct. 2, 2009, which claims priority from Patent Application No. GB 0818033.3, filed Oct. 2, 2008, the contents of which are hereby incorporated by reference.

FIELD OF THE INVENTION

The invention relates to compounds which are inhibitors of p38 mitogen-activated protein kinase enzymes (referred to herein as p38 MAP kinase inhibitors), particularly the alpha and gamma kinase sub-types thereof, and their use in therapy, especially in the treatment of inflammatory diseases, including inflammatory diseases of the lung.

BACKGROUND OF THE INVENTION

Four p38 MAPK isoforms (alpha, beta, gamma and delta respectively) have been identified, each displaying a tissue-specific expression pattern. The p38 MAPK alpha and beta isoforms are ubiquitously expressed throughout the body and are found in many different cell types. The p38 MAPK alpha and beta isoforms are inhibited by certain known small molecule p38 MAPK inhibitors. Earlier generations of compounds were highly toxic due to the ubiquitous expression pattern of these isoforms and off-target effects of the compounds. More recent inhibitors are improved to be highly selective for p38 MAPK alpha and beta isoforms and have a wider safety margin.

Less is known about the p38 MAPK gamma and delta isoforms. These isoforms are expressed in specific tissues/cells (unlike the p38 alpha and p38 beta isoforms). The p38 MAPK-delta isoform is expressed more in the pancreas, testes, lung, small intestine and kidney. It is also abundant in macrophages (Smith, S. J. (2006) *Br. J. Pharmacol.* 149:393-404) and detectable in neutrophils, CD4+ T cells and endothelial cells (www.genecard.org, Karin, K. (1999) *J. Immunol.*). Very little is known about the expression of p38 MAPK gamma but it is expressed more in brain, skeletal muscle and heart, as well as in lymphocytes and macrophages (www.genecard.org).

Selective small molecule inhibitors of p38 MAPK-gamma and -delta are not currently available, but one existing inhibitor has pan-isoform inhibitory actions. BIRB 796 inhibits all isoforms but inhibits p38 gamma and p38 delta at higher concentrations than those that inhibit p38 alpha and p38 beta (Kuma, Y. (2005) *J. Biol. Chem.* 280:19472-19479). BIRB 796 also impaired the phosphorylation of p38 MAPKs or JNKs by the upstream kinase MKK6 or MKK4. The authors discussed the possibility that the conformational change caused by the binding of the inhibitor to the MAPK may affect the structure of both its phosphorylation site and the docking site for the upstream activator, therefore impairing the phosphorylation of p38 MAPKs or JNKs.

p38 MAP kinase is believed to play a pivotal role in many of the signalling pathways that are involved in initiating and maintaining chronic, persistent inflammation in human disease, for example, severe asthma and COPD. There is now an abundant literature which demonstrates that p38 MAP kinase is activated by a range of pro-inflammatory cytokines and that its activation results in the elaboration and release of further pro-inflammatory cytokines. Indeed, data from some clinical studies demonstrate beneficial changes in disease activity in patients during treatment with p38 MAP kinase inhibitors. For instance Smith, S. J. (2006) *Br. J. Pharmacol.* 149:393-404 describes the inhibitory effect of p38 MAP kinase inhibitors on cytokine release from human macrophages. Use of inhibitors of p38 MAP kinase in the treatment of chronic obstructive pulmonary disease (COPD) is proposed. Small molecule inhibitors targeted to p38 MAPKα/β have proved to be effective in reducing various parameters of inflammation in cells and tissues, obtained from patients with COPD who are generally corticosteroid insensitive, (Smith, S. J. (2006) *Br. J. Pharmacol.* 149:393-404) and in vivo animal models (Underwood, D. C. et al. (2000) 279:895-902; Nath, P. et al. (2006) *Eur. J. Pharmacol.* 544:160-167). Irusen and colleagues also suggested the possibility of involvement of p38 MAPKα/β on corticosteroid insensitivity via reduction of binding affinity of glucocorticoid receptor (GR) in nuclei (Irusen, E. et al., (2002) *J. Allergy Clin. Immunol.*, 109:649-657). Clinical experience with a range of p38 MAP kinase inhibitors, including AMG548, BIRB 796, VX702, SCIO469 and SCIO323 is described in Lee et al. (2005) *Current Med. Chem.* 12:2979-2994.

COPD is a condition in which the underlying inflammation has been reported to be substantially resistant to the anti-inflammatory effects of inhaled corticosteroids. Consequently, an effective strategy for treating COPD my well be to develop an intervention which both has inherent anti-inflammatory effects and is able to increase the sensitivity of lung tissues from COPD patients to inhaled corticosteroids. The recent publication of Mercado et al (2007; *American Thoracic Society Abstract A56*) demonstrates that silencing p38 gamma has the potential to restore sensitivity to corticosteroids.

However, the major obstacle hindering the definition and exploitation of the potential utilities of p38 MAP kinase inhibitors in the treatment of human chronic inflammatory diseases has been the toxicity observed in patients. This has been sufficiently severe to result in the withdrawal from clinical development of many of the compounds progressed.

The compounds developed to date have typically been intended for oral administration. This strategy involves optimizing compounds which achieve their duration of action by an appropriate pharmacokinetic profile. This ensures that there is a sufficient drug concentration established and maintained after and between doses to provide clinical benefit. The inevitable consequence of this approach is that all body tissues, especially liver and gut, are likely to be exposed to therapeutically active concentrations of the drug, whether or not they are adversely affected by the disease being treated.

An alternative strategy is to design treatment approaches in which the drug is dosed directly to the inflamed organ (topical therapy). While this approach is not suitable for treating all chronic inflammatory diseases, it has been extensively exploited in lung diseases (asthma, COPD), skin diseases (atopic dermatitis and psoriasis), nasal diseases (allergic rhinitis) and gastrointestinal diseases (ulcerative colitis).

In topical therapy, efficacy can be achieved either by (i) ensuring that the drug has a sustained duration of action and is retained in the relevant organ to minimize the risks of systemic toxicity or (ii) producing a formulation which generates a "reservoir" of the active drug which is available to sustain the drug's desired effects. Approach (i) is exemplified by the anticholinergic drug tiotropium (Spiriva), which is administered topically to the lung as a treatment for COPD, and which has an exceptionally high affinity for its target receptor resulting in a very slow off rate and a consequent sustained duration of action.

There remains a need to identify and develop new compounds which are p38 MAP kinase inhibitors which have improved therapeutic potential, in particular which are more efficacious, longer acting and/or less toxic. An objective of the present invention is to provide compounds which inhibit p38 MAP kinase with certain sub-type specificity, which show good anti-inflammatory potential.

SUMMARY OF THE INVENTION

According to the invention, there is provided a compound of formula (I)

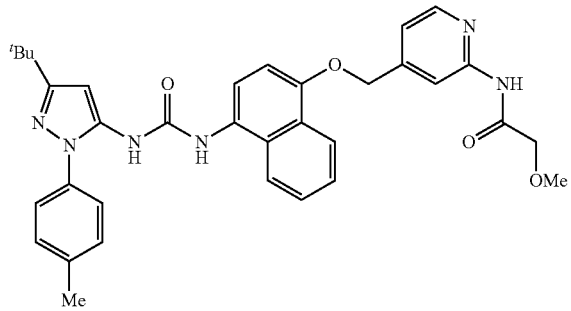

(I)

or a pharmaceutically acceptable salt or solvate thereof, including all tautomers thereof.

BRIEF DESCRIPTION OF THE FIGURES

FIG. 1 shows pre-dose time against neutrophil number in BALF for the compound of formula (I) in the LPS-induced neutrophil accumulation test.

FIG. 2 shows pre-dose time against % inhibition of neutrophilia for the compound of formula (I) in the LPS-induced neutrophil accumulation test.

FIG. 3 shows the effects of dose for the compound of formula (I) on the numbers of activated macrophages in the BAL of mice exposed to cigarette smoke.

FIG. 4 shows the effects of dose for the compound of formula (I) on numbers of neutrophils in the BAL of mice exposed to cigarette smoke.

FIG. 5 shows the effect for the compound of formula (I) on lung function of ovalbumin-sensitised, para-influenza inoculated guinea pigs challenged with ovalbumin.

DETAILED DESCRIPTION OF THE INVENTION

Examples of salts of compound (I) include acid addition salts of strong mineral acids such as HCl and HBr salts and addition salts of strong organic acids such as a methansulfonic acid salt.

The disclosure herein also extends to solvates of compounds of formula (I). Examples of solvates include hydrates.

The disclosure also extends to compounds of formula (I) where the atom specified in the formula is a naturally occurring or non-naturally occurring isotope. In one embodiment the isotope is a stable isotope. Thus the compounds of the disclosure include, for example deuterium containing compounds and the like.

A process for preparing a compound of formula (I) comprises reaction of a compound of formula (II):

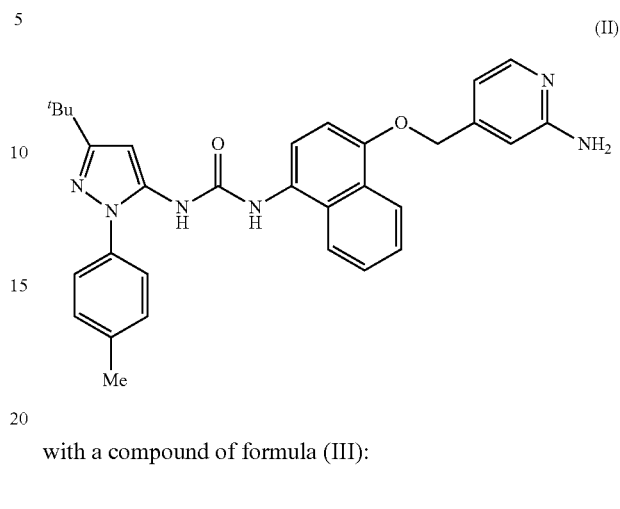

(II)

with a compound of formula (III):

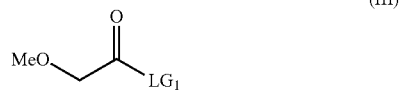

(III)

wherein $LG_1$ represents a leaving group (e.g. chloro).

The reaction is suitably carried out in the presence of a base (e.g. diisopropylethylamine). The reaction is suitably carried out in an aprotic solvent or solvent mixture, e.g. DCM and DMF.

A compound of formula (II) may be prepared by reaction of a compound of formula (IV):

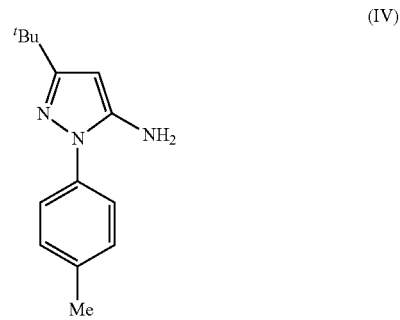

(IV)

with a compound of formula (V):

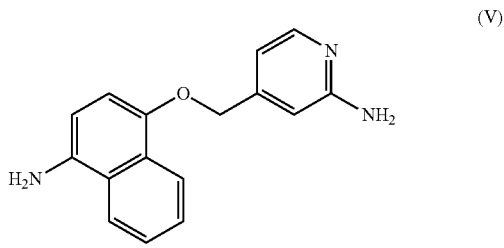

(V)

and a compound of formula (VI):

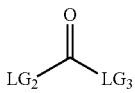

wherein $LG_2$ and $LG_3$ each independently represent leaving groups (e.g. $LG_2$ and $LG_3$ both represent imidazolyl).

The reaction is suitably carried out in an aprotic solvent (e.g. dichloromethane).

A compound of formula (V) may be prepared by reduction of a compound of formula (VII):

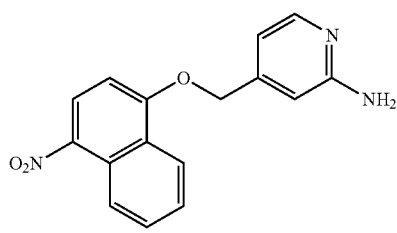

for example by hydrogenation in the presence of a catalyst such as platinum supported on carbon.

The reaction is suitably carried out in polar protic solvent (e.g. methanol and acetic acid, 1:1).

A compound of formula (VII) may be prepared by reaction of a compound of formula (VIII):

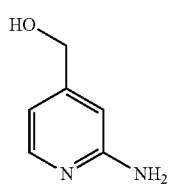

with a compound of formula (IX):

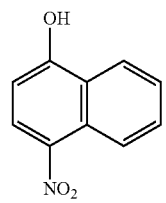

under Mitsunobu conditions, such as in the presence of triphenylphosphine and diisopropylazodicarboxylate.

The reaction is suitably carried out in a polar aprotic solvent (e.g. tetrahydrofuran).

Alternatively a compound of formula (I) may be prepared by reaction of a compound of formula (X):

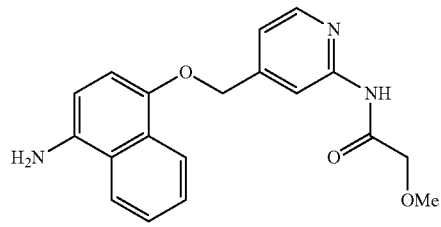

with a compound of formula (IV) defined above
and a compound of formula (XI):

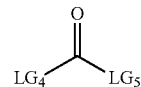

wherein $LG_4$ and $LG_5$ each independently represent leaving groups (e.g. $LG_4$ and $LG_5$ both represent imidazolyl).

The reaction is suitably carried out in a polar aprotic solvent.

A compound of formula (X) may be prepared by reduction of a compound of formula (XII):

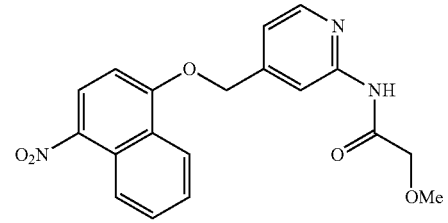

for example by hydrogenation in the presence of a catalyst, such as platinum supported on carbon.

A compound of formula (XII) may be prepared by reaction of a compound of formula (XIII):

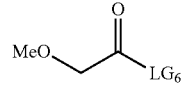

wherein $LG_6$ represents a leaving group (e.g. chloro)
and a compound of formula (VII) defined above.

The reaction is suitably carried out in the presence of a base (e.g. diisipropylethylamine). The reaction is suitably carried out in a polar solvent e.g. a mixture of DCM and DMF.

Compounds of formulae (III), (IV), (VI), (VIII), (IX), (XI) and (XIII) are either commercially available or are known and may be prepared by conventional methods. See for example Regan, J. et al.; *J. Med. Chem.*, 2003, 46, 4676-4686, WO00/043384, WO2007/087448 and WO2007/089512.

If desired or necessary, intermediate compounds may be protected by the use of conventional protecting groups. Protecting groups and means for their removal are described in "Protective Groups in Organic Synthesis", by Theodora W. Greene and Peter G. M. Wuts, published by John Wiley & Sons Inc; 4$^{th}$ Rev Ed., 2006, ISBN-10: 0471697540.

Novel intermediates are claimed as an aspect of the invention.

Further, the present invention provides a pharmaceutical composition comprising a compound of formula (I) optionally in combination with one or more pharmaceutically acceptable diluents or carriers.

Diluents and carriers may include those suitable for parenteral, oral, topical, mucosal and rectal administration.

As mentioned above, such compositions may be prepared e.g. for parenteral, subcutaneous, intramuscular, intravenous, intra-articular or peri-articular administration, particularly in the form of liquid solutions or suspensions; for oral administration, particularly in the form of tablets or capsules; for topical e.g. pulmonary or intranasal administration, particularly in the form of powders, nasal drops or aerosols, and transdermal administration; for mucosal administration e.g. to buccal, sublingual or vaginal mucosa, and for rectal administration e.g. in the form of a suppository.

The compositions may conveniently be administered in unit dosage form and may be prepared by any of the methods well-known in the pharmaceutical art, for example as described in Remington's Pharmaceutical Sciences, 17th ed., Mack Publishing Company, Easton, Pa., (1985). Formulations for parenteral administration may contain as excipients sterile water or saline, alkylene glycols such as propylene glycol, polyalkylene glycols such as polyethylene glycol, oils of vegetable origin, hydrogenated naphthalenes and the like. Formulations for nasal administration may be solid and may contain excipients, for example, lactose or dextran, or may be aqueous or oily solutions for use in the form of nasal drops or metered spray. For buccal administration typical excipients include sugars, calcium stearate, magnesium stearate, pregelatinated starch, and the like.

Orally administrable compositions may comprise one or more physiologically compatible carriers and/or excipients and may be in solid or liquid form. Tablets and capsules may be prepared with binding agents, for example, syrup, acacia, gelatin, sorbitol, tragacanth, or poly-vinylpyrollidone; fillers, such as lactose, sucrose, corn starch, calcium phosphate, sorbitol, or glycine; lubricants, such as magnesium stearate, talc, polyethylene glycol, or silica; and surfactants, such as sodium lauryl sulfate. Liquid compositions may contain conventional additives such as suspending agents, for example sorbitol syrup, methyl cellulose, sugar syrup, gelatin, carboxymethylcellulose, or edible fats; emulsifying agents such as lecithin, or acacia; vegetable oils such as almond oil, coconut oil, cod liver oil, or peanut oil; preservatives such as butylated hydroxyanisole (BHA) and butylated hydroxytoluene (BHT). Liquid compositions may be encapsulated in, for example, gelatin to provide a unit dosage form.

Solid oral dosage forms include tablets, two-piece hard shell capsules and soft elastic gelatin (SEG) capsules.

A dry shell formulation typically comprises of about 40% to 60% concentration of gelatin, about a 20% to 30% concentration of plasticizer (such as glycerin, sorbitol or propylene glycol) and about a 30% to 40% concentration of water. Other materials such as preservatives, dyes, opacifiers and flavours also may be present. The liquid fill material comprises a solid drug that has been dissolved, solubilized or dispersed (with suspending agents such as beeswax, hydrogenated castor oil or polyethylene glycol 4000) or a liquid drug in vehicles or combinations of vehicles such as mineral oil, vegetable oils, triglycerides, glycols, polyols and surface-active agents.

Suitably the compound of formula (I) is administered topically to the lung. Hence we provide according to the invention a pharmaceutical composition comprising a compound of formula (I) optionally in combination with one or more topically acceptable diluents or carriers. Topical administration to the lung may be achieved by use of an aerosol formulation. Aerosol formulations typically comprise the active ingredient suspended or dissolved in a suitable aerosol propellant, such as a chlorofluorocarbon (CFC) or a hydrofluorocarbon (HFC). Suitable CFC propellants include trichloromonofluoromethane (propellant 11), dichlorotetrafluoromethane (propellant 114), and dichlorodifluoromethane (propellant 12). Suitable HFC propellants include tetrafluoroethane (HFC-134a) and heptafluoropropane (HFC-227). The propellant typically comprises 40% to 99.5% e.g. 40% to 90% by weight of the total inhalation composition. The formulation may comprise excipients including co-solvents (e.g. ethanol) and surfactants (e.g. lecithin, sorbitan trioleate and the like). Aerosol formulations are packaged in canisters and a suitable dose is delivered by means of a metering valve (e.g. as supplied by Bespak, Valois or 3M).

Topical administration to the lung may also be achieved by use of a non-pressurised formulation such as an aqueous solution or suspension. This may be administered by means of a nebuliser. Topical administration to the lung may also be achieved by use of a dry-powder formulation. A dry powder formulation will contain the compound of formula (I) in finely divided form, typically with a mess mean diameter (MMAD) of 1-10 microns. The formulation will typically contain a topically acceptable diluent such as lactose, usually of large particle size e.g. a mass mean diameter (MMAD) of 100 μm or more, Example dry powder delivery systems include SPINHALER, DISKHALER, TURBOHALER, DISKUS and CLICKHALER.

Compounds of formula (I) are intended to have therapeutic activity. In a further aspect, the present invention provides a compound of formula (I) for use as a medicament.

Compounds of formula (I) are expected to be useful in the treatment of respiratory disorders including COPD (including chronic bronchitis and emphysema), asthma, paediatric asthma, cystic fibrosis, sarcoidosis, idiopathic pulmonary fibrosis, allergic rhinitis, rhinitis, sinusitis especially asthma, chronic bronchitis and COPD.

Compounds of formula (I) are also expected to be useful in the treatment of certain conditions which may be treated by topical or local therapy including allergic conjunctivitis, conjunctivitis, allergic dermatitis, contact dermatitis, psoriasis, ulcerative colitis, inflamed joints secondary to rheumatoid arthritis or osteoarthritis.

Compounds of formula (I) are also expected to be useful in the treatment of certain other conditions including rheumatoid arthritis, pancreatitis, cachexia, inhibition of the growth and metastasis of tumours including non-small cell lung carcinoma, breast carcinoma, gastric carcinoma, colorectal carcinomas and malignant melanoma.

Thus, in a further aspect, the present invention provides a compound of formula (I) for use in the treatment of the above mentioned conditions, for example by administering a therapeutically effective amount of said compound to a patient in need thereof.

In a further aspect, the present invention provides use of a compound of formula (I) for the manufacture of a medicament for the treatment of the above mentioned conditions.

In a further aspect, the present invention provides a method of treatment of the above mentioned conditions which comprises administering to a subject an effective amount of a compound of formula (I) or a pharmaceutical composition thereof.

The disclosure also extends to use of pharmaceutical compositions/formulations in the treatment of one or more of said conditions.

A compound of formula (I) may also be administered in combination with one or more other active ingredients e.g. active ingredients suitable for treating the above mentioned conditions. For example possible combinations for treatment of respiratory disorders include combinations with steroids (e.g. budesonide, beclomethasone dipropionate, fluticasone propionate, mometasone furoate, fluticasone furoate), beta agonists (e.g. terbutaline, salbutamol, salmeterol, formoterol) and/or xanthines (e.g. theophylline).

EXAMPLES

Example 1

N-[4-({4-[3-(3-tert-Butyl-1-p-tolyl-1H-pyrazol-5-yl)ureido]naphthalen-1-yloxy}methyl)pyridin-2-yl]-2-methoxyacetamide (1)

2-Amino-4-[(4-nitronaphthalen-1-yloxy)methyl]pyridine (3)

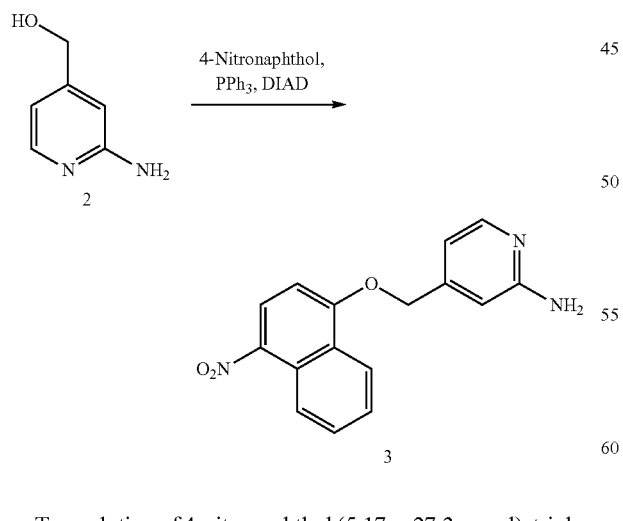

To a solution of 4-nitronaphthol (5.17 g, 27.3 mmol), triphenylphosphine (10.75 g, 41.0 mmol) and 2-aminopyridine-4-methanol (2) (5.09 g, 41.0 mmol) in THF (50 mL), at −15° C., was added dropwise diisopropyl azodicarboxylate (DIAD) (8.07 mL, 41.0 mmol). The mixture was stirred overnight at RT and the volatiles then removed in vacuo. The crude product was triturated from EtOAc (150 mL), filtered off and washed with EtOAc (100 mL). A second trituration from MeOH (100 mL) gave 2-amino-4-[(4-nitronaphthalen-1-yloxy)methyl]pyridine (3) (4.54 g, 56%) as a yellow solid: m/z 296 (M+H)$^+$ (ES$^+$).

2-Amino-4-[(4-aminonaphthalen-1-yloxy)methyl]pyridine (4)

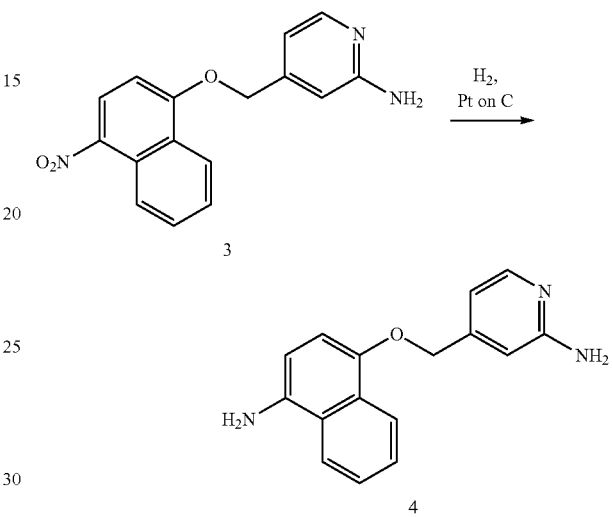

A solution of 2-Amino-4-[(4-nitronaphthalen-1-yloxy)methyl]pyridine (3) (4.50 g, 15.24 mmol) in methanol (200 mL) and glacial acetic acid (200 mL) was passed through a Thales 'H-cube' flow reactor (2 mL min$^{-1}$, 40° C., 55 mm 10% Pt/C Cat-Cart®, full H$_2$) and the volatiles were then removed in vacuo. The crude product was subjected to SCX capture and release eluting with 1% ammonia in MeOH solution and the solvent was removed in vacuo to give 2-amino-4-[(4-aminonaphthalen-1-yloxy)methyl]pyridine (4) (3.82 g, 94%) as a mauve solid: m/z 266 (M+H)$^+$ (ES$^+$).

1-{4-[(2-Aminopyridin-4-yl)methoxy]naphthalen-1-yl}-3-(3-tert-butyl-1-p-tolyl-1H-pyrazol-5-yl)urea (5)

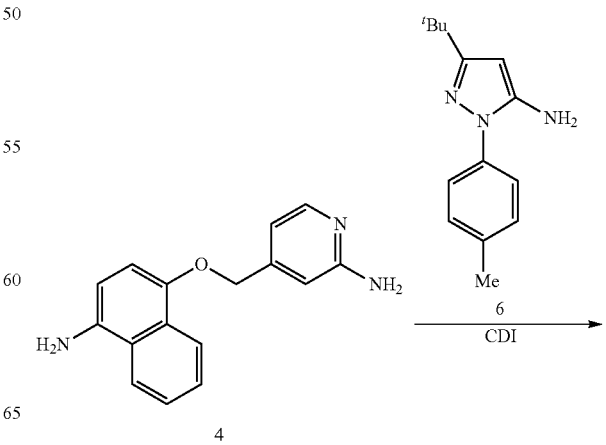

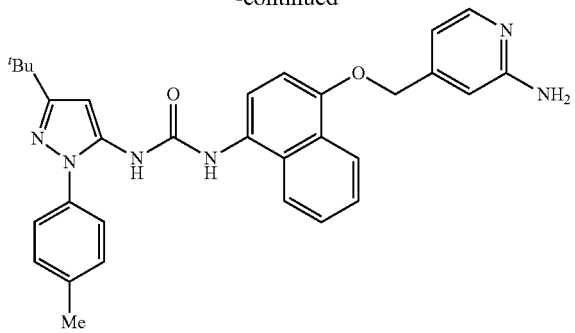

5

To a solution of 1,1'-carbonyldiimidazole (CDI) (4.18 g, 25.80 mmol) in DCM (15 mL) was added dropwise under nitrogen a solution of 3-tert-butyl-1-p-tolyl-1H-pyrazol-5-amine (6) (5.91 g, 25.80 mmol) in DCM (15 mL) over 40 mins. The resulting solution was stirred at RT for 1 h and then added dropwise under nitrogen to a solution of 2-amino-4-[(4-aminonaphthalen-1-yloxy)methyl]pyridine (4) (3.80 g, 12.89 mmol). The mixture was stirred overnight and the volatiles were then removed in vacuo. The crude material was purified by flash chromatography (Biotage 120 g); eluting with 0 to 6% MeOH in DCM to give 1-{4-[(2-aminopyridin-4-yl)methoxy]naphthalen-1-yl}-3-(3-tert-butyl-1-p-tolyl-1H-pyrazol-5-yl)urea (5) (4.27 g, 63%): m/z 521 (M+H)$^+$ (ES$^+$).

N-[4-({4-[3-(3-tert-Butyl-1-p-tolyl-1H-pyrazol-5-yl)ureido]naphthalen-1-yloxy}methyl)pyridin-2-yl]-2-methoxyacetamide (1)

To a stirred solution of 1-{4-[(2-aminopyridin-4-yl)methoxy]naphthalen-1-yl}-3-(3-tert-butyl-1-p-tolyl-1H-pyrazol-5-yl)urea (5) (526 mg, 0.96 mmol) and DIPEA (184 µL, 1.06 mmol) in mixture of DCM and DMF (10:1, 11 mL) was added methoxyacetyl chloride (92 µL, 1.01 mmol). After 1 h at RT further aliquots, of DIPEA (184 µL, 1.06 mmol) and methoxyacetyl chloride (92 µL, 1.01 mmol) were added sequentially and stirring was continued for 1 h. A solution of 1% ammonia in MeOH (40 mL), was added and the mixture stirred for 15 mins and then concentrated in vacuo. The crude product was purified by flash column chromatography (Biotage 40 g); eluting with 0 to 6% MeOH in DCM to furnish N-[4-({4-[3-(3-tert-butyl-1-p-tolyl-1H-pyrazol-5-yl)ureido]naphthalen-1-yloxy}methyl)pyridin-2-yl]-2-methoxyacetamide (1) (286 mg, 49%): m/z 593 (M+H)$^+$ (ES$^+$). $^1$H NMR (400 MHz, DMSO-d$_6$) δ: 1.27 (9H, s), 2.39 (3H, s), 3.32 (3H, s), 4.08 (2H, s), 5.39 (2H, s), 6.36 (1H, s), 7.03 (1H, d), 7.28 (1H, dd), 7.36 (2H, m), 7.44 (2H, m), 7.56-7.64 (3H, m), 7.93 (1H, m), 8.30-8.35 (3H, m), 8.58 (1H, s), 8.79 (1H, s) and 10.02 (1H, s).

Biological Testing
In Vitro Testing

| Enzyme IC$_{50}$ (nM) | | Differentiated U937 cells LPS-induced TNFα release | | THP1 cells LPS-induced |
|---|---|---|---|---|
| Alpha subtype[1] | Gamma subtype | IC$_{50}$ (nM) | MTT assay 4, 24 h (10 ug/ml) | TNFα release IC$_{50}$ (nM) |
| 5.3 | 402 | 0.88 | Negative[2] | 2.3 |

[1]p38 MAPK alpha cell based assay by detection of phosphorylation of MAPKAP-K2
[2]no significant toxic effect observed in MTT assay

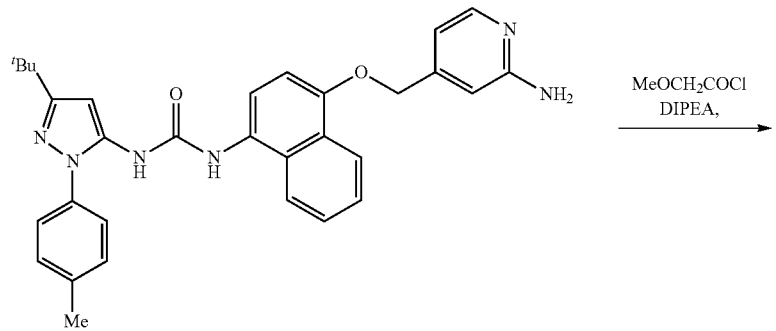

5

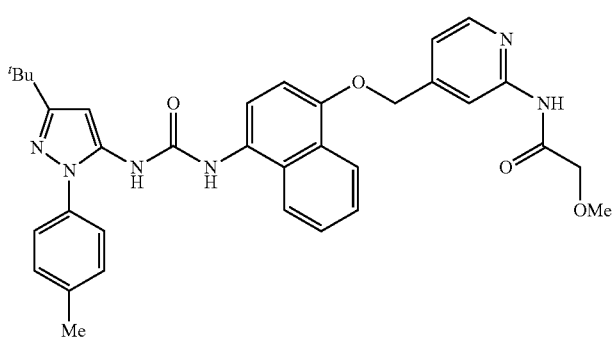

1

A description of these assays is as follows:

Enzyme Inhibition Assay

The enzyme inhibitory activity of compound was determined by fluorescence resonance energy transfer (FRET) using synthetic peptides labelled with both donor and acceptor fluorophores (Z-LYTE, Invitrogen). Briefly, recombinant, phosphorylated p38 MAPK gamma (MAPK12:Millipore) was diluted in HEPES buffer, mixed with compound at desired final concentrations and incubated for two hours at room temperature. The FRET peptide (2 uM) and ATP (100 uM) were next added to the enzyme/compound mixture and incubated for one hour. Development reagent (protease) was added for one hour prior to detection in a fluorescence microplate reader. The site-specific protease only cleaves non-phosphorylated peptide and eliminates the FRET signal. Phosphorylation levels of each reaction were calculated using the ratio of coumarin emission (donor) over fluorescein emission (acceptor) with high ratios indicating high phosphorylation and low ratios, low phosphorylation levels. The percentage inhibition of each reaction was calculated relative to non-inhibited control, and the 50% inhibitory concentration ($IC_{50}$ value) then calculated from the concentration-response curve.

For p38 MAPK alpha (MAPK14: Invitrogen), enzyme activity was evaluated indirectly by determining activation/phosphorylation of the down-stream molecule, MAPKAP-K2. The p38 MAPK α protein was mixed with its inactive target MAPKAP-K2 (Invitrogen) and compound for two hours at room temperature. The FRET peptide (2 uM), which is a phosphorylation target for MAPKAP-K2, and ATP (10 uM) were then added to the enzymes/compound mixture and incubated for one hour. Development reagent was then added and the mixture incubated for one hour before detection by fluorescence completed the assay protocol.

LPS-Induced TNF Alpha Release: Potency

U937 cells, human monocytic cell line, were differentiated to macrophage-type cells by incubation with phorbol myristate acetate (PMA; 100 ng/ml) for 48 to 72 hours. Where appropriate, cells were pre-incubated with final concentrations of compound for 2 hrs. Cells were then stimulated with 0.1 ug/ml of LPS (from *E. Coli*: O111:B4, Sigma) for 4 hrs, and the supernatant collected for determination of TNFα concentration by sandwich ELISA (Duo-set, R&D systems). THP-1, human monocytic cell line, was also used for this assay. THP-1 cells were stimulated with 1 ug/ml of LPS (from *E. Coli*: O111:B4, Sigma) for 4 hrs, and the supernatant collected for determination of TNFα concentration. The percentage inhibition of TNFα production was calculated at each concentration of test compound by comparison with vehicle control, and the 50% inhibitory concentration value ($IC_{50}$) was determined from the resultant concentration-response curve.

MTT Assay

Differentiated U937 cells were pre-incubated with compound for 4 hrs in 5% FCS or 10% FCS for 24 hrs and 72 hrs. The supernatant was replaced with 200 ul of new media and 10 ul of MTT stock solution (5 mg/ml) added to each well. After 1 hr incubation, the media were removed, 200 ul of DMSO added to each well and the plates were shaken lightly for 1 hour prior to reading the absorbance at 550 nm.

The percentage loss of cell viability was calculated for each well relative to vehicle (0.5% DMSO)-treatment. Consequently an apparent increase in cell viability for drug treatment relative to vehicle is tabulated as a negative percentage.

In Vivo Testing

LPS-Induced Neutrophilia in the Mouse

Non-fasted mice were dosed by the intra tracheal route with either vehicle, or the test substance at the time points ("pre-dose") indicated with respect to the start of LPS treatment. At T=0, mice were placed into an exposure chamber and exposed to LPS. 8 hours after LPS challenge, animals were under anesthetized, the trachea cannulated and BALF extracted by infusing and withdrawing 1 ml of PBS into the lungs via a tracheal catheter. Total and differential white cell counts in the BALF samples were measured using a Neubaur haemocytometer. Cytospin smears of the BALF samples were prepared by centrifugation at 200 rpm for 5 min at room temperature and stained using a DiffQuik stain system (Dade Behring). Cells were counted using oil immersion microscopy.

The results are shown in FIGS. 1 and 2. Data for neutrophil numbers is reported as total and differential number (test substance relative to vehicle) of cells per mL of BALF, mean±S.E.M. (n=8).

Cigarette Smoke Model

A/J mice (males, 5 weeks old) were exposed to cigarette smoke (4% cigarette smoke, diluted with compressed air) for 30 min/day for 11 days using a Tobacco Smoke Inhalation Experiment System for small animals (Model SIS-CS; Sibata Scientific Technology, Tokyo, Japan). Test substances were given intra-nasally (35 µl of solution in 50% DMSO/PBS) and therapeutically twice daily for 3 days after the final cigarette smoke exposure. Twelve hours after the last dosing, animals were anesthetized, the trachea cannulated and bronchoalveolar lavage fluid (BALF) was collected. The numbers of alveolar macrophages and neutrophils were determined by FACS analysis (EPICS® ALTRA II, Beckman Coulter, Inc., Fullerton, Calif., USA) using anti-mouse MOMA2 antibody (macrophage) or anti-mouse 7/4 antibody (neutrophil).

The results are shown in FIG. 3 for activated alveolar macrophages and in FIG. 4 for neutrophils. Data for cell numbers are shown as the mean±SEM. The cigarette smoke model used for this study is reported as a corticosteroid refractory system, (Medicherla S. et al., (2008); J. Pharmacol. Exp. Ther. 324(3):921-9) and it was confirmed that fluticasone propionate did not inhibit either neutrophil or macrophage accumulation into airways at 50 µg/ml (35 µl, bid, m), the same dose that produced >80% inhibition of LPS-induced neutrophil accumulation.

In FIG. 3:

Significant difference between air exposure and cigarette smoke exposure.

***P<0.001 vs. cigarette smoke (CS) control (ANNOVA, Dunnett's multiple comparison), n=6-11

In FIG. 4:

Significant difference between air exposure and cigarette smoke exposure.

*P<0.05 or ***P<0.001 vs. cigarette smoke (CS) control (ANNOVA, Dunnett's multiple comparison), n=6-11

Ovalbumin Challenge/Parainfluenza Infection Model (In Vivo Model for Steroid Resistance)

Male Dunkin-Hartley guinea-pigs (300-350 g, n=6/group) were sensitised with 100 µg ovalubumin (OVA)+100 mg $Al_2(OH)_3$ in 1 ml normal saline (i.p.) on days 2 and 6. Parainfluenza virus (PIV-3; $10^6$ infectious units) or media without virus was nasally instilled on days 11 and 12. Animals were treated with nebulised fluticasone propionate at a dose of 1.5 mg per day. Initial studies established that this dose of fluticasone propionate inhibited ovalbumin-mediated lung function changes in sensitized animals treated with PIV3 medium. Example 1 (4.5 mg per day) or the vehicle (DMSO:ethanol:

saline, 30:30:40%) from days 10-15. All animals were challenged for 1 h with nebulised OVA (10 μg/ml) on day 15 and repeated measurements of specific airways conductance ($sG_{aw}$) were made over a 24 h period using whole body plethysmography. Measurements of $sG_{aw}$ after OVA challenge are plotted as % change from baseline. See FIG. 5.

FIG. 5 Data are shown as the mean of 6 observations; (○) PIV3+vehicle treatment; (■) PIV3+fluticasone propionate treatment; (▲) PIV3+Example 1 treatment Summary The biological studies in vitro show that the compound of formula (I) is a potent inhibitor of p38 MAP kinase subtypes alpha and gamma with good efficacy in an in vitro model of anti-inflammatory activity (LPS-induced TNFalpha release from differentiated U937 cells and THP-1 cells). From the MTT results it may be concluded that the compound does not exhibit overt cellular toxicity at the concentrations used.

The biological studies in vivo show that the compound of formula (I) is effective in inhibiting LPS-induced neutrophil accumulation in an animal model, with a long duration of effect as shown by the significant inhibition even at 12 or more hours of pre-dosing. Furthermore, the compound of formula (I) has been shown to be effective in two in vivo models of steroid-resistant inflammation.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

All patents and patent applications referred to herein are incorporated by reference in their entirety.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the claims.

ABBREVIATIONS

| | |
|---|---|
| Ac | acyl |
| ATP | Adenosine-5'-triphosphate |
| BALF | Bronchoalveolae lavage fluid |
| BSA | bovine serum albumin |
| CatCart ® | catalytic cartridge (brand name) |
| CDI | carbonyldiimidazole |
| DCM | dichloromethane |
| DIAD | diisopropyl azodicarboxylate |
| DMF | dimethylformamide |
| DMSO | dimethyl sulfoxide |
| COPD | chronic obstructive pulmonary disease |
| DIAD | diisopropyl azodicarboxylate |
| DIBAL-H | diisobutylaluminium hydride |
| DIPEA | N-ethyl-N-isopropylpropan-2-amine |
| Et | ethyl |
| FCS | foetal calf serum |
| h | hour(s) |
| HRP | horseradish peroxidase |
| JNK | c-Jun N-terminal kinase |
| MAPK | mitogen protein activated protein kinase |
| Me | methyl |
| PBS | phosphate buffered saline |
| PPh₃ | triphenylphosphine |
| RT | room temperature |
| SCX | solid supported cation exchange |
| SDS | sodium dodecyl sulfate |

-continued

| | |
|---|---|
| TFA | trifluoroacetic acid |
| THF | tetrahydrofuran |
| TNFα | tumor necrosis factor alpha |
| TMB | 3.3', 5.5'-tetramethylbenzidine |
| MTT | 3-(4,5-Dimethylthiazol-2-yl)-2,5-diphenyltetrazolium bromide |

The invention claimed is:

1. A compound of formula (I)

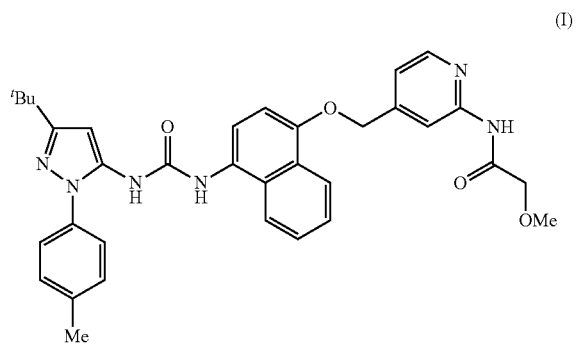

or a pharmaceutically acceptable salt or solvate thereof, including all tautomers thereof.

2. A pharmaceutical composition comprising a compound according to claim 1, in combination with one or more pharmaceutically acceptable diluents or carriers.

3. A method of treatment of a condition selected from the group consisting of COPD, asthma, paediatric asthma, cystic fibrosis, sarcoidosis, idiopathic pulmonary fibrosis, allergic rhinitis, rhinitis, sinusitis, allergic conjunctivitis, conjunctivitis, allergic dermatitis, contact dermatitis, psoriasis, ulcerative colitis, inflamed joints secondary to rheumatoid arthritis or osteoarthritis, rheumatoid arthritis, pancreatitis, and cachexia, which comprises administering to a subject in need thereof an effective amount of a compound of formula (I) according to claim 1.

4. A process for preparation of a compound of formula (I) or a pharmaceutically acceptable salt or solvate thereof, including all tautomers thereof which comprises reaction of a compound of formula (II):

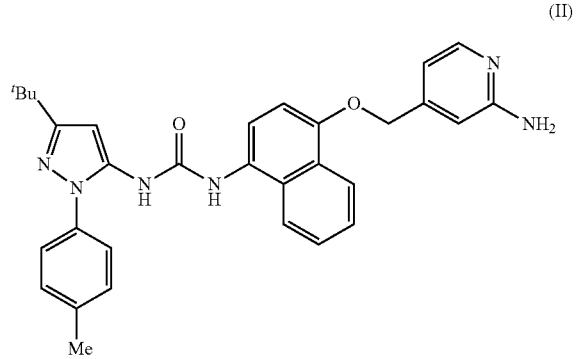

with a compound of formula (III):

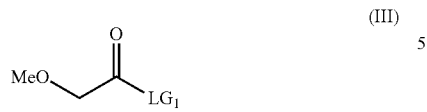
(III)

wherein LG₁ represents a leaving group.

5. A process for preparation of a compound of formula (I) or a pharmaceutically acceptable salt or solvate thereof, including all tautomers thereof which comprises reaction of a compound of formula (X):

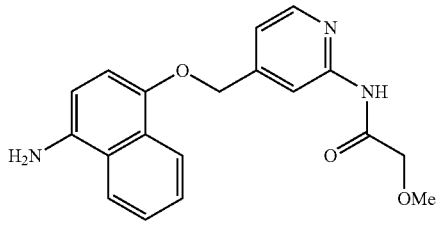
(X)

with a compound of formula (IV):

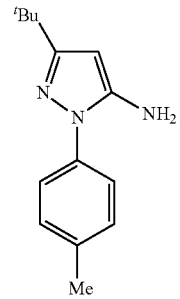
(IV)

and a compound of formula (XI):

(XI)

wherein LG₄ and LG₅ each independently represent leaving groups.

6. A compound of formula (X):

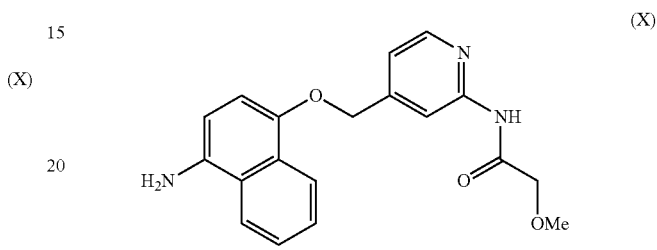
(X)

or a salt thereof.

7. A method of treatment of a condition selected from the group consisting of COPD, asthma, paediatric asthma, cystic fibrosis, sarcoidosis, idiopathic pulmonary fibrosis, allergic rhinitis, rhinitis, sinusitis, allergic conjunctivitis, conjunctivitis, allergic dermatitis, contact dermatitis, psoriasis, ulcerative colitis, inflamed joints secondary to rheumatoid arthritis or osteoarthritis, rheumatoid arthritis, pancreatitis, and cachexia, which comprises administering to a subject in need thereof a pharmaceutical composition according to claim 2.

8. A method according to claim 7, wherein the condition is selected from the group consisting of COPD, asthma, paediatric asthma, cystic fibrosis and allergic rhinitis.

9. A method according to claim 3, wherein the condition is selected from the group consisting of COPD asthma, paediatric asthma, cystic fibrosis and allergic rhinitis.

* * * * *